United States Patent [19]

Posner et al.

[11] Patent Number: 5,668,013
[45] Date of Patent: Sep. 16, 1997

[54] ANTIGEN RECOGNIZED BY PATIENTS WITH ANTIBODY ASSOCIATED PARANEOPLASTIC CEREBELLAR DEGENERATION, DNA ENCODING SAME AND USES THEREOF

[75] Inventors: Jerome B. Posner; Henry M. Furneaux, both of New York, N.Y.

[73] Assignee: Sloan-Kettering Institute for Cancer Research, New York, N.Y.

[21] Appl. No.: 427,993

[22] Filed: Apr. 24, 1995

Related U.S. Application Data

[63] Continuation of Ser. No. 646,292, Jan. 25, 1991, abandoned.
[51] Int. Cl.[6] .................. C12N 15/12; C12N 15/62; C12N 14/435; C12N 14/82; C12N 1/21
[52] U.S. Cl. .................. 435/320.1; 435/693; 435/252.3; 536/23.5; 530/350; 530/395; 530/402; 530/828
[58] Field of Search .................. 435/69.3, 252.3, 435/320.1; 536/23.5; 530/350, 395, 402, 828

[56] References Cited

FOREIGN PATENT DOCUMENTS 0297585  1/1989  European Pat. Off. ........ C12N 15/00

OTHER PUBLICATIONS

Fathallah–Shaykh et al (91) Proc. Natl. Acad. Sci USA 88:3451–3454.
Sakai, K et al. (90) Ann. Neurol. 28:692–698.
Sato, S. et al (91) Biochem. Biophys. Res. Comm. 178: 198–206.
Short, JM. et al. (88) Nucl. Acids Res. No.: 7583–7599.
Furneaux, H.M. et al (89) Proc. Natl. Acad. Sci USA 86:2873–2877.
Cunningham, JM et al. (86) Neurology 36:1163–1168.
Anderson, NE et al. (88a) Neurology 38:1018–1026.
Anderson, NE. et al. (88b) Ann. Neurology 24:559–567.
Tsukamoto, T. et al. (89) Arch. Neurol. 46:1225–1229.
Furneaux, H.M. et al. (90) Neurology 40 (Suppl. 1) p. 166 Abstract #1805.
Dropcho, E.J. et al (87) Proc. Natl. Acad. Sci. USA 84:4552–4556.
Mierendorf, R.C. et al. (87) Meth. Enzym. 152:458–469.
Young, R.A. et al. (83) Proc. Natl. Acad. Sci USA 80:1194–1198.
Bowie, J. et al. Science 247: 1306–1310 (1990).
Kumar, V. et al. Proc. Natl. Acad. Sci USA 87: 1337–1341 (1990).
Anderson, N.E., et al. (1988) "Autoantibodies in paraneoplastic syndromes associated with small–cell lung cancer." *Neurology* 38: 1391–1398 (Exhibit 2).

Brain, L. and Wilkinson, M. (1965) "Subacute cerebellar degeneration associated with neoplasms." *Brain* 88: 465–478 (Exhibit 3).
Darnell, R., et al. (1989) "Characterization of neural antigens recognized by autoantibodies in CSF and serum of a patient with cerebellar degeneration: co–expression in Purkinje cells and tumor lines of neuroectodermal origin." *Neurology* 39 (Suppl.1): 385 (Exhibit 4).
Furneaux, H.M., et al. (1990) "Selective expression of Purkinje cell antigens in tumor tissue from patients with paraneoplastic cerebellar degeneration." *New Eng. J. Med.* 322: 1844–1851 (Exhibit 5).
Gentz, R., et al. (1989) "Parallel Association of Fos and Jun leucine zippers juxtaposes DNA binding domains." *Science* 243: 1695–1699 (Exhibit 6).
Greenlee, J.E., et al. (1983) "Antibodies to cerebellar Purkinje cells in patients with paraneoplastic cerebellar degeneration and ovarian carcinoma." *Annals of Neurology* 6: 609–613.
Jaeckle, K.A., et al. (1988) "Autoimmune response of patients with paraneoplastic degeneration to a Purkinje cell cytoplasmic antigen." *Annals of Neurology* 18: 592–600 (Exhibit 7).
Janson, J.–C. (1984) "Large–scale affinity purification–state of the art and future prospects." *Trends in Biotechnology* 2: 31–38 (Exhibit 9).
Lampson, L. (1987) "Molecular bases of the immune response to neural antigens." *Trends Neurosci.* 10: 211–216 (Exhibit 10).
Rodriguez, M., et al. (1988) "Autoimmune paraneoplastic cerebellar degeneration: ultrastructural localization of antibody–binding sites in Purkinje cells." *Neurology* 38: 1380–1386 (Exhibit 11).
Vinson, C., et al. (1989) "Scissors–grip model for DNA recognition by a family of leucine zipper proteins." *Science* 246: 911–916 (Exhibit 12).

*Primary Examiner*—Anthony C. Caputa
*Attorney, Agent, or Firm*—John P. White

[57] ABSTRACT

An isolated nucleic acid sequence encoding major Yo paraneoplastic antigenic polypeptide is provided by this invention. This invention also provides a purified major Yo antigenic polypeptide and compositions containing the purified major Yo antigenic polypeptide. Further provided by this invention is a monoclonal antibody directed to an epitope on the major Yo paraneoplastic antigenic polypeptide. Compositions containing this monoclonal antibody also are provided by this invention. This invention also provides methods of diagnosis and treatment using the compositions described hereinabove.

8 Claims, 12 Drawing Sheets

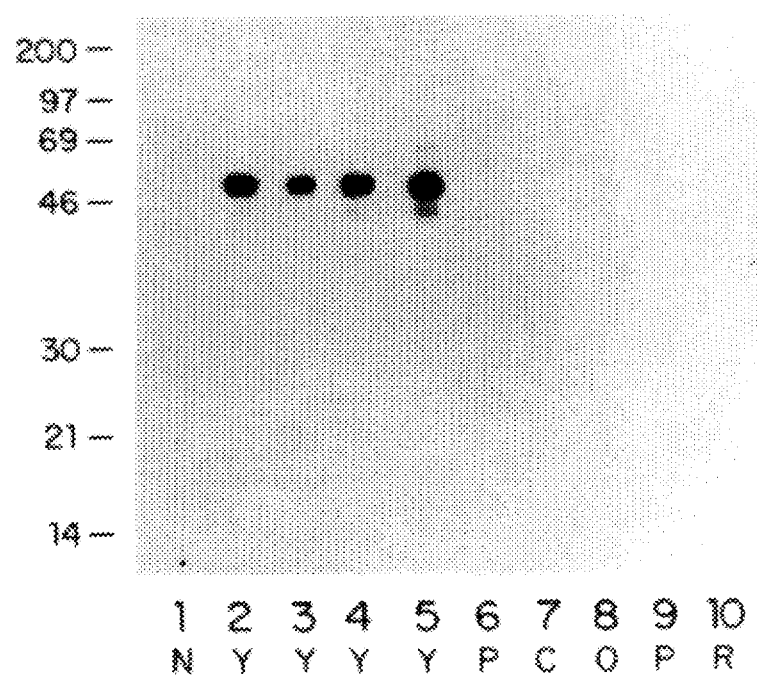

FIG. 5

```
                  20                         40                         60
                   *                          *                          *
        SAAGPNGAEAAQRSLGGGAS      RPRAALAEGGGAGEEPGAAA      EAGRRRGPLPLEDPAEMLAE 80                        100                        120
                   *                          *                          *
        NLVEEFEMKEDEPWYDHQDL      QQDLQLAAELGKTLLDRNTE      LEDSVQQMYTTNQEQLQEIE

>LEUZIP
                                                        |
                 140                        160         |              180
                   *                          *         |                *
        YLTKQVELLRQMNEQHAKVY      EQLDVTARELEETNQKLVAD      SKASQQKILSLTETIECLQT
                                                                            ●            ●

200                        220                        240
                   *                          *                          *
        NIDHLQSQVEELKSSGQGRR      SPGKCDQEKPAPSFACLKEL      YDLRQHFVYDHVFAEKITSL
            ●              ●

260                        280                        300
                   *                          *                          *
        QGQPSPDEEENEHLKKTVTM      LQAQLSLERQKRVTMEEEYG      LVLKENSELEQQLGATGAYR 320                        340                        360
                   *                          *                          *
        ARALELEAEVAEMRQMLQSE      HPFVNGVEKLVPDSLYVPFK      EPSQSLLEEMFLTVPESHRK 380                        400                        420
                   *                          *                          *
        PLKRSSSETILSSLAGSDIV      KGHEETCIRRAKAVKQRGIS      LLHEVDTQYSALKVKYEELL 440                        460                        480
                   *                          *                          *
        KKCQEEQDSLSHKAGRPPGC      SQGPDWSDAQSEPVASGWEL      ASVNPEPVSSPTTPPEYKAL

500
                   *
        FKEIFSCIKKTKQEIDEQRT      KYRSLSSHS
```

FIG. 7A

```
                20                              40                              60
                 *                               *                               *
TCCCCGCAAGATCTTCAACT    TGCTGCTGAGCTTGGGAAGA    CATTACTGGATCGGAACACA
 S  P  Q  D  L  Q  L     A  A  E  L  G  K        T  L  L  D  R  N  T>

80                             100                             120
                 *                               *                               *
GAGTTGGAGGACTCTGTTCA    GCAGATGTATACAACCAATC    AGGAGCAGTTACAGGAAATT
 E  L  E  D  S  V  Q     Q  M  Y  T  T  N        Q  E  Q  L  Q  E  I>

140                             160                             180
                 *                               *                               *
GAGTATCTGACGAAGCAAGT    GGAACTTCTACGGCAGATGA    ACGAACAACATGCAAAGGTT
 E  Y  L  T  K  Q  V     E  L  L  R  Q  M        N  E  Q  H  A  K  V>

200                             220                             240
                 *                               *                               *
TATGAACAATTAGACGTCAC    AGCAAGGGAACTGGAAGAAA    CAAATCAAAAGCTAGTTGCT
 Y  E  Q  L  D  V  T     A  R  E  L  E  E        T  N  Q  K  L  V  A>

260                             280                             300
                 *                               *                               *
GACAGCAAGGCCTCACAGCA    AAAGATTCTGAGCCTGACTG    AAACGATTGAATGCCTGCAA
 D  S  K  A  S  Q  Q     K  I  L  S  L  T        E  T  I  E  C  L  Q>

320                             340                             360
                 *                               *                               *
ACCAACATTGATCACCTCCA    GAGCCAAGTGGAGGAGCTGA    AGTCATCTGGCCAAGGGAGA
 T  N  I  D  H  L  Q     S  Q  V  E  E  L        K  S  S  G  Q  G  R>

380                             400                             420
                 *                               *                               *
AGGAGCCCGGGAAAGTGTGA    CCAGGAGAAACCGGCACCCA    GCTTTGCATGTCTGAAGGAG
 R  S  P  G  K  C  D     Q  E  K  P  A  P        S  F  A  C  L  K  E>

440                             460                             480
                 *                               *                               *
CTGTATGACCTCCGCCAACA    CTTCGTGTATGATCATGTGT    TCGCTGAGAAGATCACTTCC
 L  Y  D  L  R  Q  H     F  V  Y  D  H  V        F  A  E  K  I  T  S>
```

FIG. 7B

```
              500                      520                      540
               *                        *                        *
TTGCAAGGTCAGCCAAGCCC  TGATGAAGAGGAAAATGAGC  ACTTGAAAAAAACAGTGACA
 L  Q  G  Q  P  S  P    D  E  E  N  E      H  L  K  K  T  V  T>

560                      580                      600
               *                        *                        *
ATGTTGCAGGCCCAGCTGAG  CCTGGAGCGGCAGAAGCGGG  TGACTATGGAGGAGGAATAT
 M  L  Q  A  Q  L  S    L  E  R  Q  K  R    V  T  M  E  E  E  Y>

620                      640                      660
               *                        *                        *
GGGCTCGTGTTAAAGGAGAA  CAGTGAACTGGAGCAGCAGC  TGGGGGCCACAGGTGCCTAC
 G  L  V  L  K  E  N    S  E  L  E  Q  Q    L  G  A  T  G  A  Y>

680                      700                      720
               *                        *                        *
CGAGCACGGGCGCTGGAACT  AGAGGCCGAGGTGGCAGAGA  TGCGACAGATGTTGCAGTCA
 R  A  R  A  L  E  L    E  A  E  V  A  E    M  R  Q  M  L  Q  S>

740                      760                      780
               *                        *                        *
GAGCATCCATTTGTGAATGG  AGTTGAGAAGCTGGTGCCAG  ACTCTCTGTATGTTCCTTTC
 E  H  P  F  V  N  G    V  E  K  L  V  P    D  S  L  Y  V  P  F>

800                      820                      840
               *                        *                        *
AAAGAGCCCAGCCAGAGCCT  GCTGGAAGAGATGTTCCTGA  CTGTGCCGGAATCACATAGA
 K  E  P  S  Q  S  L    L  E  E  M  F  L    T  V  P  E  S  H  R>

860                      880                      900
               *                        *                        *
AAGCCTCTCAAGCGCAGCAG  CAGTGAGACGATCCTCAGCA  GCTTGGCAGGGAGTGACATC
 K  P  L  K  R  S  S    S  E  T  I  L  S    S  L  A  G  S  D  I>

920                      940                      960
               *                        *                        *
GTGAAGGGCCACGAGGAGAC  CTGCATCAGGAGGGCCAAGG  CTGTGAAACAGAGGGGCATC
 V  K  G  H  E  E  T    C  I  R  R  A  K    A  V  K  Q  R  G  I>
```

FIG. 7C

```
            980                      1000                      1020
             *                        *                         *
TCCCTTCTGCACGAAGTGGA   CACGCAGTACAGCGCCCTGA   AGGTGAAGTATGAAGAGTTG
 S  L  L  H  E  V  D    T  Q  Y  S  A  L      K  V  K  Y  E  E  L>

1040                     1060                      1080
             *                        *                         *
CTGAAGAAGTGCCAAGAGGA   ACAGGACTCCCTGTCACACA   AGGCTGGCAGACCTCCAGGC
 L  K  K  C  Q  E  E    Q  D  S  L  S  H      K  A  G  R  P  P  G>

1100                     1120                      1140
             *                        *                         *
TGCAGCCAAGGACCTGACTG   GAGTGACGCCCAGTCTGAGC   CTGTTGCCAGCGGCTGGGAA
 C  S  Q  G  P  D  W    S  D  A  Q  S  E      P  V  A  S  G  W  E>

1160                     1180                      1200
             *                        *                         *
CTGGCCTCTGTCAACCCAGA   GCCCGTGAGTTCCCCTACAA   CACCTCCAGAATACAAAGCG
 L  A  S  V  N  P  E    P  V  S  S  P  T      T  P  P  E  Y  K  A>

1220                     1240                      1260
             *                        *                         *
TTGTTTAAGGAGATCTTTAG   TTGCATCAAGAAAACTAAGC   AGGAAATAGATGAACAGAGA
 L  F  K  E  I  F  S    C  I  K  K  T  K      Q  E  I  D  E  Q  R>

1280                     1300                      1320
             *                        *                         *
ACAAAATACCGATCACTCTC   CTCTCATTCTTAATTGACCT   CTAGCTCTACTACTAATTTG
 T  K  Y  R  S  L  S    S  H  S>

1340                     1360                      1380
             *                        *                         *
CCTATTGCCTATCGCCTCTC   TCCCATTCAGACAAGTGTTT   GTAGACTCTGAAGCCTAATG 1400                     1420                      1440
             *                        *                         *
TTACTCATGACGTTTGCCTC   ATTGCTTTGCTTATTTAGCA   AATGCATACAACGAGGAAAG
```

FIG. 7D

```
               1460                    1480                    1500
                 *                       *                       *
GAGGTGGCTAGTGGTATCAG    TTCTCTGATCCACTTCCATT    TAACCTCCCCAGGAAATCCC 1520                    1540                    1560
                 *                       *                       *
ATGACAAACTGGCCTCTGGC    TGGCGCGCTGATTAGACTTC    AGTTCCTGAAAAGGACCAGT 1580                    1600                    1620
                 *                       *                       *
GGAGGGAAGAGCTATACTTC    TGGAGAAGTAGGCCTGGAGT    TACTACAGTATGGGGGAAAA 1640                    1660                    1680
                 *                       *                       *
GGGTCGAGTTAGAACAAAGC    TAAGGCAATTCCTATTGCTT    CCTTGCGCAACTTCTCAAAA 1700                    1720                    1740
                 *                       *                       *
CGATGAAAGTCAGAAGGCTG    TCAAACTCAAATATCTTTGC    AAACACTGTTTGAATACTGT 1760                    1780                    1800
                 *                       *                       *
GAATTCTTCATTACGAAGAA    TGTTCGAGAGAAAGCAGGGG    TCTAATCCAAAAGAAATGTC 1820                    1840                    1860
                 *                       *                       *
ATTAACCAATACTCCAAGTC    CTTGAGTTTTGTTATATCTG    AACTAGTTGAACTGTGACTG 1880                    1900                    1920
                 *                       *                       *
ACAGGTAATCCTAATATATC    CAAATCCAACTGAATACCAA    ATTGAGATGGCAAATTTTTG
```

FIG. 7E

```
            1940                    1960                    1980
              *                       *                       *
TTTGATATAAGTTAGCTTGT    TAGCATATGCCCTAGAGGGC    CTCCATCCCTGATTCTAATG 2000                    2020                    2040
              *                       *                       *
TTTTTACTCAAAGCTCTAGC    CTTTAGGATAGGTGAATATG    TAAATCTTTTATCACTTTCT 2060                    2080                    2100
              *                       *                       *
CAAATTCAAACTAAAGGGGA    AAGATCAAACCCCTTCCCTT    CCTACCTGTTTTCTGAGCTG 2120                    2140                    2160
              *                       *                       *
GCTGACTTGCCAGCCACAAG    CTGCTCTTGCAGAGTTCTTA    CCATTCCTGTAAATGTTTTG 2180                    2200                    2220
              *                       *                       *
ACTTGTTGCAGAAATTCCTA    TCTACTTTATTAAGCAGTAT    TGATCTGACTGTGGAAACAT 2240                    2260                    2280
              *                       *                       *
CCTCTCACTTGCATTCTTTT    AACTTAAAACTATTTAAGAA    CTGATGTTCCGATTATTGTA 2300                    2320
              *                       *
TATATTTTTCTAAAAACCAA    ATAAAGCTACCTATGAAAGG    AATTCCGGAATTC
```

5,668,013

ANTIGEN RECOGNIZED BY PATIENTS WITH ANTIBODY ASSOCIATED PARANEOPLASTIC CEREBELLAR DEGENERATION, DNA ENCODING SAME AND USES THEREOF

This is a continuation of application Ser. No. 07/646,292, filed Jan. 25, 1991, now abandoned.

This invention was made with support under Grant Number CA08748 from the National Institute of Health. Accordingly, the United States government has certain rights to the invention.

BACKGROUND OF THE INVENTION

Throughout this application various references are referred to within parentheses. Disclosures of these publications in their entirety are hereby incorporated by reference into this application to more fully describe the state of the art to which this invention pertains. Full bibliographic citations for these references maybe found at the end of this application, immediately preceding the claims.

Paraneoplastic cerebellar degeneration (PCD) is a disorder of the cerebellum found in association with neoplasms usually of lung, ovary, breast, or Hodgkins disease. [1] Neuropathological analysis of the affected brains has revealed extensive loss of Purkinje cells, variable loss of granule and basket neurons and proliferation of Bergman glia. [2] The mechanistic relationship between the primary tumor and the resultant cerebellar dysfunction is not clearly understood. The presence of infiltrating lymphocytes in some of the affected brain has suggested an immune mechanism. [3]

A clinically definable subset of patients with paraneoplastic cerebellar degeneration harbor a characteristic antibody which has been called anti-Yo [4]. These sera react with antigens expressed in the Purkinje cells of the normal cerebellum and in the tumor tissue of the affected individual [5]. There is also evidence of increased antibody synthesis in the affected brain. [6]

These observations suggest a model for the neurological dysfunction in which an immune response primarily directed against a tumor antigen is misdirected against similar antigens peculiar to the cerebellum. On Western blot analysis of Purkinje cells and tumor tissue, the anti-Yo sera react with at least two antigens, a major species of 62 kd (CDR 62) and a minor species of 34 kd (CDR 34). [7] Anti-Yo antibody has been detected in patients prior to discovery of the tumor. [19] In four of these patients, prior radiological investigations had disclosed minor abnormalities of uncertain significance. Detection of this antibody prompted surgical exploration and biopsy disclosed a tumor in each case.

The gene encoding the minor antigen (CDR 34) has been isolated and characterized [8,9]. In addition, a cDNA encoding a 52-kd protein has been isolated, recognized by an antineuronal cell antibody in serum from a patient with PCD associated with uterine carcinoma. [18] However, specificity of reaction between the protein encoded by this isolated cDNA and Yo sera was not established. [18]

SUMMARY OF THE INVENTION

An isolated nucleic acid sequence encoding major Yo paraneoplastic antigenic polypeptide is provided by this invention. This invention also provides a purified major Yo antigenic polypeptide and compositions containing the purified major Yo antigenic polypeptide.

A method of detecting an antibody associated with paraneoplastic cerebellar degeneration (PCD) is provided by this invention. This method comprises contacting a suitable sample with the purified major Yo antigenic polypeptide labelled with a detectable marker under conditions so as to form a complex between the purified major Yo antigenic polypeptide and the antibody, detecting the presence of any complex so formed, thereby detecting an antibody associated with paraneoplastic cerebellar degeneration.

Also provided by this invention is a method of determining whether a patient exhibiting neurological symptoms has paraneoplastic cerebellar degeneration (PCD) or harbors a tumor expressing major Yo antigen, which comprises contacting a suitable sample from the patient with the major Yo antigenic polypeptide, the polypeptide being labeled with a detectable marker, under suitable conditions so as to form a complex between the antibody and the polypeptide, detecting the presence of any complex so formed, the presence of complex being a positive determination that the patient has a tumor which expresses a major Yo antigen or PCD.

A method of inhibiting the proliferation of neoplastic cells in a patient having paraneoplastic cerebellar degeneration (PCD) also is provided by this invention. This method comprises administering to the patient an effective amount of a monoclonal antibody directed to the major Yo paraneoplastic antigenic polypeptide, the monoclonal antibody being labeled with a therapeutic agent, in an amount which is effective to inhibit the proliferation of the neoplastic cells, thereby inhibiting the proliferation of neoplastic cells in a patient having PCD.

This invention further provides a method of imaging neoplastic cells in a patient, wherein the neoplastic cells are associated with paraneoplastic cerebellum degeneration (PCD), which comprises administering to the patient an effective amount of a monoclonal antibody directed to major Yo paraneoplastic antigen, the monoclonal antibody being labelled with an imaging agent, under conditions to form a complex between the monoclonal antibody and an antigenic polypeptide associated with PCD, imaging any complex so formed, thereby imaging neoplastic cells in a patient.

Figure 1:
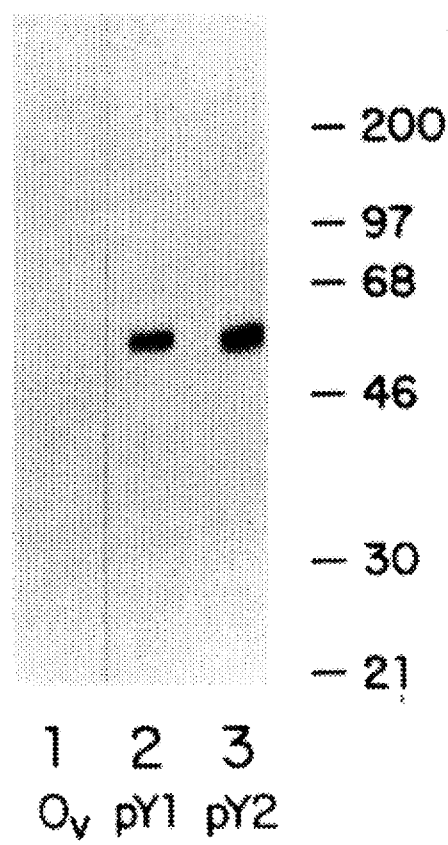
FIG. 1—Epitope selection analysis of pY1, pY2. Nitrocellulose filters containing fusion protein encoded by pY1, pY2 and as a control a β-galactosidase-ovalbumin fusion protein were incubated with anti Yo sera (5 µg/ml) for 2 hours at room temperature. After washing with TBST, the IgG fraction bound to the filter was eluted with 0.1M Na Citrate (pH 2.5). The purified IgG was then re-reacted with Western blot nitrocellulose strips containing protein from human Purkinje cells. Lane 1, negative contral eluate from ovalbumin fusion protein. Lane 2 eluate from pY1. Lane 3 eluate from pY2.

(A) Protein extracts (50 µg total protein) from pBS (parental plasmid containing no insert) and pY2 were resolved by SDS 10% Acrylamide gel electrophoresis, transferred to nitrocellulose and incubated with anti Yo sera (lanes 1,2).

(B) The fusion protein encoded by pY2 was purified by preparative SDS—10% acrylamide gel electrophoresis. The partially purified protein was then run on a "curtain

3 well" SDS-polyacrylamide gel, transferred to nitrocellulose and cut into strips of equal size. Strips (containing equal amounts of fusion protein) were then incubated with lane 1, normal human sera, lanes 2, 3, 4, 5 anti Yo positive sera and lanes 6–10 anti Yo negative sera.

Figure 4:
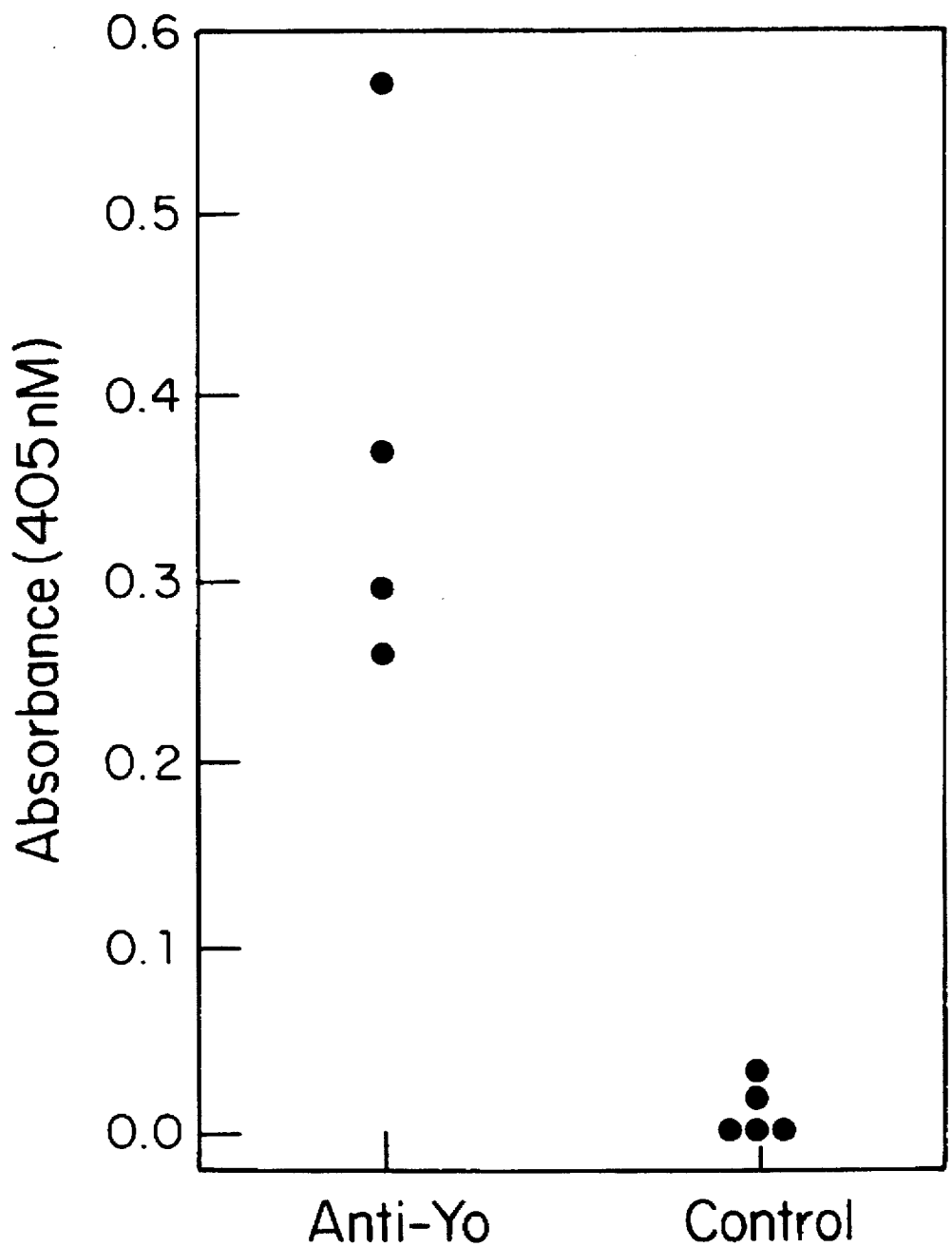

FIG. 4—Elisa Assay using pY2 Fusion Protein Partially purified pY2 fusion protein was immobilized to 96 well microtitre plates and serum reactivity assayed as described in materials and methods. Each dot on the two Y axes correspond to a single determination.

FIG. 5—The composite open reading frame specified by pY1 pY2 is shown in single letter amino acid code. The leucine zipper domain is shown and the participating leucine residues highlighted. Seq. ID No. 1.

Figure 6:
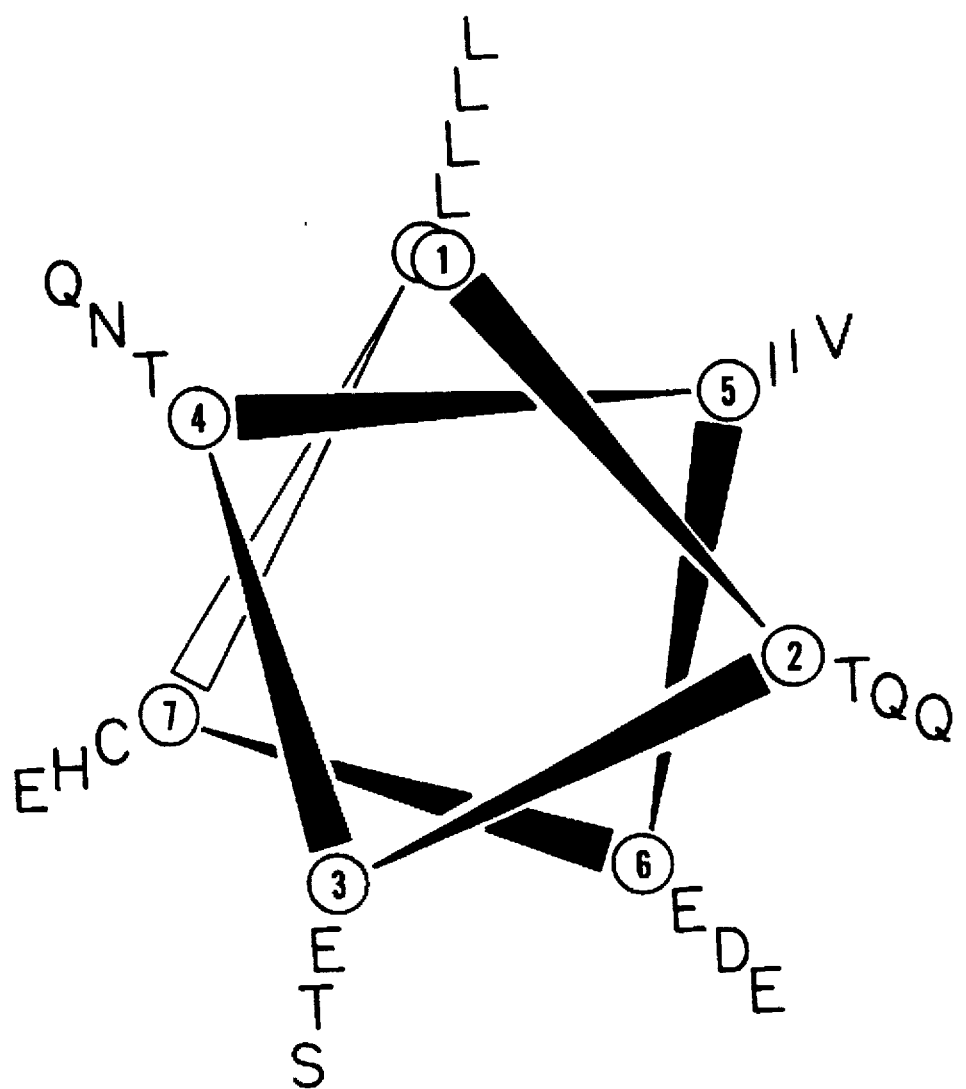

FIG. 6—Helical wheel analysis of leucine zipper domain. The analysis starts with leu (171) and ends at leucine (192). The helical wheel consists of seven spokes corresponding to the fit of seven amino acids into every two α helical turns. The single letter amino acid code is used.

FIGS. 7A–E—cDNA sequence (Seq. ID No.2) and amino acid sequence (Seq. ID No.1) of major Yo antigenic polypeptide of this invention. Seq. ID No. 2.

DETAILED DESCRIPTION OF THE INVENTION

This invention provides an isolated nucleic acid sequence encoding major Yo paraneoplastic antigenic polypeptide. As used herein, the term major Yo paraneoplastic antigenic polypeptide encompasses any amino acid sequence having the biological activity of major Yo antigenic protein, i.e., a protein which may specifically form a complex with an antibody which is characteristic of paraneoplastic cerebellar degeneration. This antibody has also been called anti-Yo. This antibody, i.e., anti-Yo, is characteristically found in patients with paraneoplastic cerebellar degeneration, a disorder of the cerebellum found in association with neoplasms of lung and breast. This antigenic major Yo polypeptide is approximately 62 kd.

In one embodiment of this invention, the isolated nucleic acid sequence described hereinabove is DNA. In another embodiment of this invention, the isolated nucleic acid sequence described hereinabove is cDNA, or it is RNA. In the preferred embodiment of this invention, the isolated nucleic acid sequence is a cDNA sequence as shown in FIGS. 7A–E.

A vector which comprises the isolated nucleic acid molecule described hereinabove also is provided. Suitable vectors comprise, but are not limited to, a plasmid or a virus. This vector may be transfected into a suitable host cell to form a host vector system for the production of a polypeptide having the biological activity of the major Yo antigenic polypeptide.

This invention further provides an isolated DNA or cDNA molecule described hereinabove wherein the host cell is selected from the group consisting of bacteria cells such as E. coli, yeast and fungi cells, insect cells and animal cells. Suitable animal cells include, but are not limited to Vero cells, HeLa cells, Cos cells , CV1 cells and primary mouse cells.

Further provided by this invention is a method for producing a polypeptide having the biological activity of the major Yo antigenic polypeptide comprising the steps of: a) culturing the host vector system described hereinabove under suitable conditions permitting production of the polypeptide and b) recovering the polypeptide produced. This invention also provides the polypeptide produced by this method.

4

Throughout this application, references to specific nucleotides are to nucleotides present on the coding strand of the nucleic acid. The following standard abbreviations are used throughout the specification to indicate specific nucleotides:

| C = cytosine | A = adenosine |
| T = thymidine | G = guanosine |
| U = uracil | |

This invention also encompasses DNAs and cDNAs which encode amino acid sequences which differ from those of the major Yo paraneoplastic antigenic polypeptide, but which should not produce phenotypic changes. Alternatively, this invention also encompasses DNAs and cDNAs which hybridize to the DNA and cDNA of the subject invention. Hybridization methods are well known to those of ordinary skill in the art. This invention also encompasses cDNA and DNA molecules characterized by changes in non-coding regions that do not alter the phenotype of the polypeptide produced.

Also provided by this invention is a purified, major Yo antigenic polypeptide. The purified major Yo antigenic polypeptide may be labeled with a detectable marker. For the purposes of this invention, suitable detectable markers include, but are not limited to detectable markers selected from the group consisting of radioisotopes, dyes, enzymes and biotin.

This invention further provides a monoclonal antibody directed to an epitope on the major Yo antigenic polypeptide. In one embodiment of this invention, the monoclonal antibody is a mouse monoclonal antibody. In another embodiment of this invention, the monoclonal antibody is a human monoclonal antibody.

For the isolation of mouse monoclonal antibodies, eight week old mice may be injected interperitoneally with about 50 micrograms of a synthetic, purified major Yo antigenic polypeptide, (prepared as described above) in complete Freud's adjuvant 1:1 volume. Mice will then be boosted, at monthly intervals, with the polypeptide, mixed with incomplete Freund's adjuvant, and bled through the tail vein. On days 4, 3, and 2 prior to fusion, mice will be boosted intravenously with 50 micrograms of the polypeptide in saline. Splenocytes will then be fused with non-secreting myeloma cells according to procedures which have been described and are known to those of ordinary skill in the art to which this invention pertains. Some time later, approximately two weeks later, hybridoma supernatant will then be screened for binding activity against the major Yo antigenic polypeptide as described hereinafter. Positive clones will then be isolated and propagated.

In addition, this invention also provides the monoclonal antibody described hereinabove conjugated to a therapeutic agent. For the purposes of this invention, suitable therapeutic agents include, but are not limited to, a therapeutic agent selected from the group consisting of radioisotopes, toxins, toxoids, and chemotherapeutic agents. Also provided by this invention is the monoclonal antibody described hereinabove conjugated to a detectable marker. Suitable detectable markers include, but are not limited to, enzymes, radioisotopes, dyes and biotin. This invention further provides monoclonal antibodies as described hereinabove conjugated to an imaging agent. Suitable imaging agents include, but are not limited to radioisotopes, such as, $^{32}$P, $^{35}$S, and $^{131}$I.

Also provided by this invention are pharmaceutical compositions comprising the purified, major Yo antigenic polypeptide described hereinabove alone, or conjugated to any one of the following: a detectable marker, a therapeutic agent, or an imaging agent, as described hereinabove and a pharmaceutically acceptable carrier. Further provided are pharmaceutical compositions comprising the monoclonal antibody described hereinabove alone, or conjugated to any one of the following: a detectable marker, a therapeutic agent, or an imaging agent. As used herein, the term "pharmaceutically acceptable carrier" encompasses any of the standard pharmaceutical carriers, such as phosphate buffered saline solution, water, emulsions, such as a oil/water emulsions, and various types of wetting agents.

A method of detecting an antibody associated with paraneoplastic cerebellar degeneration "PCD", i.e., the major Yo antigenic protein, is also provided by this invention. This method comprises contacting a suitable sample with a purified major Yo antigenic polypeptide described hereinabove under conditions so as to form a complex between the purified major Yo antigenic polypeptide and the antibody, detecting the presence of any complex so formed, thereby detecting an antibody associated with paraneoplastic cerebellar degeneration. Suitable samples include any sample suspected containing an antibody associated with PCD, such as serum or cerebral-spinal fluid. In one embodiment of the invention the synthetic purified major Yo antigenic polypeptide is labeled with a detectable marker selected from the group consisting of radioisotopes, dyes, enzymes and biotin. For the purposes of this invention, suitable radioisotopes include, but are not limited to, $^{32}P$, $^{35}S$, and $^{131}I$.

Also provided by this invention is a method of determining whether a patient exhibiting neurological symptoms harbors a tumor expressing the Yo antigen, which comprises obtaining the suitable sample from the patient, contacting the suitable sample with a monoclonal antibody directed against the Yo antigen, under conditions so as to form a complex between the antibody and the Yo antigen, detecting the presence of any complex so formed, the presence of a complex being a positive determination that the patient harbors a tumor expressing the Yo antigen. In one embodiment of this invention, the monoclonal antibody is labeled with a detectable marker. For the purposes of this invention, suitable detectable markers include, but are not limited to a detectable marker selected from the group consisting of radioisotopes, dyes, enzymes and biotin. Suitable radioisotopes have been described hereinabove.

Further provided by this invention is a method of inhibiting the proliferation of neoplastic cells in a patient having paraneoplastic cerebellar degeneration. This method comprises administering to the patient an effective amount of the monoclonal antibody or composition described hereinabove conjugated to a therapeutic agent, in an amount which is effective to inhibit the proliferation of neoplastic cells, and under suitable conditions so as to form a complex between an antigen associated with the neoplasm and the monoclonal antibody thereby inhibiting the proliferation of neoplastic cells. As used herein, an effective amount is any amount which is effective to inhibit the proliferation of neoplastic cells. As is known to those of ordinary skill in the art, effective amounts vary with the type of therapeutic agent utilized, as well the neoplastic cell tumor being treated. It is well known to those of ordinary skill in the art how to determine an effective amount of a suitable therapeutic agent.

As used herein, "administering" means a method of administering to the patient. Such methods are well known to those skilled in the art and include, but are not limited to administration orally, intravenously, or parenterally. Administration of the agent may be effected continuously or intermittently, such that the amount of the therapeutic agent in the patient is effective to inhibit proliferation of neoplastic cells. For the purposes of this invention suitable therapeutic agents include radioisotopes, toxins, toxoids, and chemotherapeutic agents.

Also provided by this invention is a method of imaging neoplastic cells in a patient, wherein the neoplastic cells are associated with paraneoplastic cerebellar degeneration. The method comprises administering to the patient the monoclonal antibody described hereinabove which is labelled with an imaging agent, for example $^{131}I$, or a composition containing the same, and administered it to the patient to bind to a major Yo antigen present on or within the neoplastic cells so as to form a complex between the monoclonal antibody and the antigen, detecting any complex so formed, thereby imaging neoplastic cells in a patient associated with PCD, or neoplastic cells expressing Yo antigen. As is well known to those of ordinary skill in the art, a suitable amount of monoclonal antibody or composition is any amount which is effective to image the neoplastic cells, for example, about 0.1 mCi to about 50.0 mCi. In addition, an effective amount of the monoclonal antibody may be an amount from about 0.01 mg to about 100 mg. Suitable methods of administering the imaging agent are as described hereinabove.

Imaging of any complex so formed may be carried out using single photon computed emission tomography (SPECT) or by using a gamma camera.

Materials and Methods

Materials

Sera from patients with antibody associated paraneoplastic cerebellar degeneration was obtained from the patients' physicians. A Hela cell λ ZAP expression library was obtained from Stratagene.

Methods

Screening of λ Hela Expression Library

Recombinant phage were screened at a density of $2\times10^4$ pfu per 150 mm plate of E. coli XLI-Blue. After incubation for 6 hours at 37° C. the plates were overlaid with filters soaked in IPTG (10 mM) and incubated for a further 12 hours at 37° C. The filters were then removed and incubated with anti Yo sera (2 µg/ml IgG) for 2 hours at room temperature. The filters were then washed with TBST (50 mM Tris (pH 7.4), 100 mM NaCl, 0.2% Triton) and incubated with $I^{125}$ Protein A. After washing with TBST the filters were exposed to XRA5 film at −70° C. Clones yielding positive signals were purified by several rounds of antibody screening until 100% of the plaques gave positive signals.

Analysis of Fusion Proteins

Phage clones were subcloned into p Bluescript (pBs) using the phage rescue protocol. [10] Individual clones were grown to an optical density of 0.6 and induced by adding IPTG (10 mM). After 1 hour of induction at 37° C. the bacterial cells were isolated by centrifugation and lysed by the addition of 2% SDS Laemlli buffer. E coli lysates were then resolved by 8% polyacrylamide SDS gel electrophoresis and transferred to nitrocellulose [11]. The filters were then incubated with anti-Yo sera (5 µg/ml in TBST) for 2 hours at room temperature. The filters were then washed with TBST and incubated with $I^{125}$ protein A. After a further washing with TBST, the filters were exposed to XRA5 film at −70° C.

Northern Blot Analysis

Total RNA was prepared from Hela cells using the guanidinium hydrochloride phenol-chloroform extraction method. The RNA was separated by 1.2% Agarose/ formaldehyde gel electrophoresis and transferred to Hybond N according to the manufacturers specification. The Hybond N filter was prehybridized with 50% Formamide, 5×SSPE, 0.05% PVP 0.05% Ficoll, 200 µg/ml denatured DNA. Probe was synthesized from clone pY2 using T7 RNA polymerase and $^{32}$P UTP. [10] The filter was hybridized with probe ($10^7$ cpm/ml) in prehybridization buffer at 55° C. The filter was then washed with 0.1×SSC/0.1% SDS at 60° C. and exposed to XRA5 film.

DNA Sequence Analysis

All sequencing was based on the dideoxy termination method [10]. Double stranded DNA was sequenced on both strands using SK, KS, M13 universal and reverse primers, and internal oligonucleotide primers. Sequences were merged and analyzed for open reading frame and functional motifs with the Macvector analysis software.

Elisa Assay

Partially purified preparations of the fusion protein encoded by pY2 were absorbed to 96 well microliter plates. After blocking reactive sites with 2% BSA/PBS, the wells were incubated with the appropriate concentration of sera diluted in 1% goat serum (2 hours at room temperature). Reactivity was determined by incubation with biotinylated goat anti-human IgG, (1/1000) followed by avidin-biotin peroxidase complex. Peroxidase was measured by oxidation of OPD and absorbance was measured at 402 nm.

Results

Isolation of Positive λ Clones

In order to clone the major Yo antigen (CDR 62) five libraries were obtained. Five were screened and found to be negative. Screening of a Hela cell λ ZAP II expression library with a typical high-titer anti-Yo sera resulted in the isolation of two consistently positive clones (y1, y2). None of these clones were recognized by normal human sera. The two clones were further analyzed by the epitope selection method. In this procedure, the antibodies that recognize the recombinant fusion protein are isolated and reacted with a Western blot of the tissue antigen. Purified antibodies from bona-fide clones should identify the original antigen of interest. FIG. 1 (lanes 3,4) shows that affinity purified antibodies selected by reactivity with the fusion proteins encoded by clones y1 and y2 recognized CDR 62 expressed in human Purkinje neurons. A mock purification of anti-Yo sera employing an irrelevant fusion protein served as the negative control (FIG. 1, lane 1). Both clones were related and encoded CDR 62.

Figure 2:
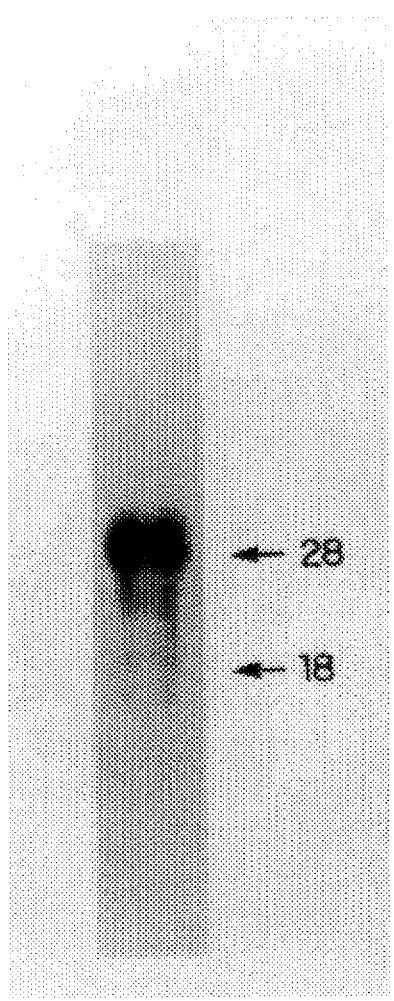
FIG. 2—Northern blot of HeLa RNA. Total RNA was extracted from HeLa cells and separated by 1.2% Formaldehyde-Agarose gel electrophoresis. The filter was incubated with [$^{32}$p] RNA probe, washed and exposed to XRA5 film for 4 hours at −70° C.

Both λ phage clones were then subcloned into PBS utilizing the phagemid rescue procedure. The resulting bacterial plasmids pY1, pY2 had inserts of 0.8 kb and 2.3 kb respectively. Restriction enzyme digestion and hybridization analysis confirmed that the two clones were related and overlapped. A similar antibody screen was conducted using a human cerebellar library. Four independent clones were isolated and found to be related to pY1 and pY2. These clones were not analyzed further. Northern blot analysis of Hela total RNA with probe synthesized from pY2 revealed an abundant transcript of 51K. (FIG. 2)

Plasmid pY2 was deposited on Jan. 25, 1991 with the American Type Culture Collection (ATCC), 12301 Parklawn Drive, Rockville, Md. 20852, U.S.A. under the provisions of the Budapest Treaty for the International Recognition of the Deposit of Microorganisms for the Purposes Of Patent Procedure. Plasmid pY2 was accorded ATCC Accession Number 40948.

Specific Recognition of cDNA Clones by Anti-Yo Sera

Figure 3A:
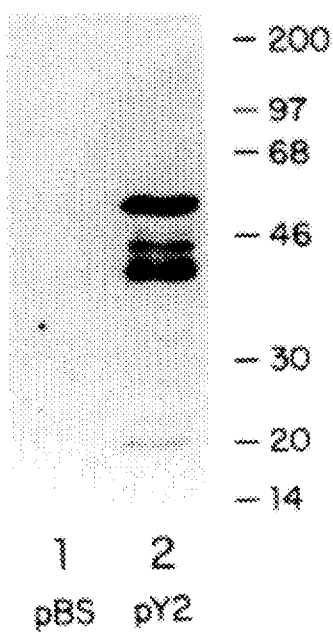
FIGS. 3A and B—Anti Yo sera specifically react with pY2 fusion protein.

Preliminary experiments revealed that the fusion protein encoded by pY2 was the most reactive with anti-Yo sera. This clone was therefore the reagent of choice to establish a quantitative diagnostic assay. The reactivity of anti-Yo sera and various negative control sera was established by Western blot analysis of the fusion protein encoded by pY2. Anti-Yo sera identify a fusion protein of 55 kd in extracts of pY2. No reactivity was observed with extracts of PBS (the parental plasmid vector with no insert). (FIG. 3A, lane 2). FIG. 3B shows that reactivity with sera previously characterized as anti-Yo were positive (lanes 2,3,4,5,). Negative controls included; normal human sera (lane 1), sera from patients with cerebellar degeneration due to the causes (lane 7), patients with ovarian tumors (lane 8) and patients with ovarian tumors, PCD but no anti-Yo antibody (lanes 6,9) and serum from a different antibody associated paraneoplastic syndrome (lane 10).

In a separate study, four false positive sera were distinguished by recombinant assay utilizing the antigen of the subject invention.

Elisa Assay for Anti-Yo Sera

The routine assay for the detection of anti-Yo antibodies involves immunohistochemical and Western blot analysis of human cerebellar tissue. Sera are defined as anti-Yo if they react specifically with Purkinje cells and identify a major species of 62 kd on Western blot analysis. Western blot analysis is essential since other sera which react with Purkinje cells but do not identify a 62 kd protein have been encountered. [12] This assay is currently conducted by research laboratories. Screening for this antibody in a large patient population will require a simpler diagnostic assay. Towards this end we have established an Elisa assay based on the recombinant CDR 62 antigen. Partially purified preparations of the pY2 fusion protein were immobilized on 96 well microliter plates and reacted with the same group of sera utilized in FIG. 3B. All four anti-Yo sera were clearly positive whereas all negative sera were not significantly different than background. (FIG. 4).

Sequence Analysis of pY1, pY2

Sequence analysis of pY2 revealed a large open reading frame of 431 amino acids which was in frame with the AUG of β galactosidase. The predicted molecular weight of this open reading frame (54 kd) agrees well with that observed in FIG. 3(A). Sequence analysis of pY1 confirmed that it overlapped with the 5' end of pY2 and provided another 243 nucleotides of 5' sequence. Together pY1 and pY2 yielded a composite open reading frame of 509 amino acids. (FIG. 5 Seq ID No. 1). It has not yet been established that the N terminal AUG. Secondary structure analysis revealed a highly hydrophilic protein with extensive regions of α-Helix. The most conspicuous feature was a leucine zipper motif found at residues 171 to 192. This motif, consisting of a heptad repeat of leucine residues forming an amphiphillic α-Helix, is a distinctive feature of proteins which bind to DNA as a hetero or homodimer. [13, 14] The amphiphillic nature of the leucine zipper found in CDR62 is illustrated in a helical wheel analysis (FIG. 6). A thin ridge of hydrophobicity is evident down the axis of the putative α Helix. In addition allowing the substitution of serine (164) and histidine (137) a "super" leucine zipper stretches from residues 122 to 170 in complete register with the leucine zipper at 171 to 192. Helical wheel analysis of the "super" leucine zipper also revealed a clear hydrophobic ridge down the axis of the α Helix. Preliminary experiments have shown that CDR62 can in fact bind to DNA. Assaying CDR62 by Western blot we have shown that the protein present in cytoplasmic extracts of Hela cells binds strongly to native DNA-cellulose. (Fathallah & Furneaux, data not shown). CDR62 does not appear to contain the characteristic basic DNA binding domain found in many leucine zipper proteins. It should be noted however, the presence of two putative DNA binding motifs (a SPKK site (Seq ID No. 3) at codon 201 and a Zinc Finger at codons 205–231) adjacent to the leucine zipper. Also consistent with the function of the protein as a transcription factor is the presence of a highly acidic (pI=3.4) activating domain between residues 52 and 80. Leucine zipper proteins in general display little homology in the amino acids found between the leucine residues. In this case it was noted that the almost perfect homology between a leucine zipper element found in CD62 (LQTNIDHL-amino acids 178 to 185 of Seq ID No. 1) to that found in the leucine zipper present in C-Fos [15] Seq ID No. 4.

Discussion

A human expression library and isolated cDNA clones that encode an epitope recognized by the sera of patients were screened with antibody associated PCD. On the basis of the epitope selection analysis it has been concluded that these cDNAs correspond to the major antigen CDR62. There is a possibility that the cDNAs encode an epitope shared with CDR62 but do not correspond to the protein itself. Antibodies specifically raised against the fusion protein will definitively answer this question. Irrespective of the true identity of the cDNAs; they encode an antigenic species which is uniquely recognized by anti-Yo sera. In contrast to the previously cloned minor antigen (CDR34) the fusion proteins encoded by the present cDNAs are highly reactive with anti-Yo sera (detectable binding is observed at 0.2 µg/ml of IgG.). The fusion protein encoded by these clones, provides the most sensitive assay for the detection of anti-Yo sera.

The most conspicuous structural feature of CDR62 is a leucine zipper motif. The presence of this feature and of putative DNA binding domains is beleived to indicate that this protein plays a role in the regulation of gene expression. It will be crucial to isolate the DNA sequence recognized by CDR62. The similarity of the leucine zipper element between CDR62 and Cos. It is conceivable that CDR62 may interact with the same family of proteins that interact with C-Fos. [15] There is no obvious similarity between CDR62 and the previously cloned minor antigen CDR34. They are clearly different gene products, CDR34 resides on chromosome X (4) whereas CDR62 resides on chromosome 16. CDR34 is an unusual protein consisting almost entirely of tandem repeats to a six amino acid consensus sequence l/FLEDVE Seq ID Nos:5 and 6). Such tandem repetition gives rise to a number of single (L-L) zipper elements. We speculate that anti-Yo sera specifically recognizes leucine zipper elements. This speculation is fuelled by the recent isolation (from an expression library) of another gene product (CD III) which contains a leucine zipper element.

It is hypothesized that the pathological mechanisms of the syndrome are that cerebellar dysfunction arises from an immune response directed against the cerebellum but provoked by the aberrant expression of the neural antigen in tumor tissue. There is no direct proof of this model. Injection of anti-Yo antibodies into experimental animals have failed to reproduce the syndrome. The availability of the recombinant CDR62 antigen will permit the generation of an appropriate immune response in experimental animals and hopefully create an animal model. In addition, the specific expression of CDR62 in patient's tumor samples can now be examined. The other fascinating aspect of this syndrome is that these patients made an extremely exaggerated immune response to their tumor tissue. Tumor tissue (presumably the CDR62 antigen) is clearly perceived as foreign by the patients' immune system. There are at least two models which may help us to understand this phenomenon. Firstly it may be that the CDR62 protein is normally restricted in its expression to brain tissue. The brain is an immunologically privileged site. [16, 17] The implication is that the expression of a brain protein in extra-neural tumor tissue may provoke an intense immune response. In the second model we suggest that the CDR62 antigen is expressed normally in extra-neural tissue but it undergoes a somatic mutation. In view of the highly hydrophilic α helical structure of CDR62, it is reasonable to suppose that even a single amino acid change may drastically affect the structure of the protein. The abnormal epitopes thus created may result in CDR62 being perceived as foreign by the immune system. An underlying corollary is that the mutation in CDR62 would have to be a clonal event. This would imply that mutation in CDR62 is a necessary event for tumor progression. With the cloned CDR62 in hand these models can now be tested.

References

1. Henson, R. and Urich, H. "Cancer and the nervous system." 1982 Blackwell Scientific. Oxford.
2. Brain, L. and Wilkinson, M. 88: 465–478, 1965.
3. Furneaux, H. and Posner, J. Paraneoplastic neurological syndromes. Proc. Assoc. Res. Nerv. Men. Dis. 68: 187–219, 1990.
4. Anderson, N. E., Rosenblum, M. K., Graus, F., Wiley, R. G. and Posner, J. B. Autoantibodies in paraneoplastic syndromes associated with small-cell lung cancer. Neurology 38: 1391–1398, 1988.
5. Furneaux, H., Rosenblum, M., Dalmau, J., Wong, E., Woodruff, P., Graus, F. and Posner, J. Selective expression of Purkinje cell antigens in tumor tissue from patients with paraneoplastic cerebellar degeneration. New Eng. J. Med. 322: 1844–51, 1990.
6. Furneaux, H., Reich, L. and Posner, J. Central nervous system synthesis of autoantibodies in paraneoplastic syndromes. Neurology. 40: 1085–1091, 1990.
7. Cunningham, J., Graus, F., Anderson, N. and Posner, J. Partial characterization of the Purkinje cell antigens in paraneoplastic cerebellar degeneration. Neurol. 36: 1163–1168, 1986.
8. Dropcho, E., Chen, Y., Posner, J. and Old, L. Cloning of a brain protein identified by autoantibodies from a patient with paraneoplastic cerebellar degeneration. Proc. Nat. Acad. Sci. 84: 1987.
9. Furneaux, H., Dropcho, E., Barbut, D., Chen, Y.-T., Rosenblum, M., Old, L. and Posner, J. Characterization of a cDNA encoding a 34 kd Purkinje neuron protein recognized by sera from patients with paraneoplastic cerebellar degeneration. Proc. Natl. Acad. Sci, USA. 86: 2873–2877, 1989.
10. Maniatis, T., Fritsch, B. and Sambrook, J. "Molecular cloning: a laboratory manual." 1982 Cold Spring Harbor, N.Y.
11. Towbin, H., Staehelin, T. and Gordon, J. A procedure for the electrophoretic transfer of proteins from polyacrylamide gels to nitro cellulose sheets. Proc. Nat. Acad. Sci. 76: 4350–4352, 1979.
12. Darnell, R., Furneaux, H. and Posner, J. Characterization of neural antigens recognized by autoantibodies in CSF and serum of a patient with cerebellar degeneration: co-expression in Purkinje cells and tumor lines of neuroectodermal origin. Neurology. 39(Suppl.1): 385, 1989.
13. Landschulz, W., Johnson, P. and McKnight, S. Science. 240: 1759, 1988.
14. Vinson, C., Sigler, P. and McKnight, S. Scissors-grip model for DNA recognition by a family of leucine zipper proteins. Science. 246: 911–916, 1989.

15. Gentz, R., Rauscher, F. I., Abate, C. and Curran, T. Science. 243: 1695–1699, 1989.
16. Lampson, L. Molecular bases of the immune response to neural antigens. Trends Neurosci. 10: 211–6, 1987.
17. Medawar, P. Immunity to homologous grafted skin III the fate of skin homografts transplanted to the brain, to subcutaneous tissue, and to the anterior chamber of the eye. Br. J. Exp. Pathol. 29: 58–69, 1948.
18. Sakai, K. et al. Isolation of a complementary DNA clone encoding an autoantigen recognized by an anti-neuronal cell antibody from a patient with paraneoplastic cerebellar degeneration. Annals of Neurology. 28 (5): 692–698, 1990.
19. Anderson, N. E. et al. Paraneoplastic cerebellar degeneration: clinical-immunological correlations. Annals of Neurology. 24 (4): 559–567, 1988.

What is claimed is:

1. An isolated nucleic acid which comprises the nucleic acid sequence set forth in Seq. ID No. 2, wherein said isolated nucleic acid encodes for a polypeptide.

2. The isolated nucleic acid of claim 1, wherein the isolated nucleic acid is cDNA.

3. A vector which comprises an isolated nucleic acid encoding a polypeptide having the amino acid sequence set forth in Seq. ID No. 1.

4. The vector of claim 3, wherein the vector is a plasmid.

5. The plasmid pY2 (ATCC Accession Number 40948).

6. The vector of claim 3, wherein the vector is a virus.

7. A fusion protein which comprises a portion of the Yo antigen, wherein the amino acid sequence of said portion is set forth in Seq. ID No. 1.

8. A fusion protein expressed by the plasmid pY2 (ATCC Accession Number 40948).

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
  ( A ) LENGTH: 509 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: N ( i v ) ANTI-SENSE: N ( v ) FRAGMENT TYPE: N-terminal ( v i i ) IMMEDIATE SOURCE:
  ( A ) LIBRARY: Hela cell library
  ( B ) CLONE: pY1pY2

( x i ) SEQUENCE DESCRIPTION: SEQ ID NO:1:

```
Ser  Ala  Ala  Gly  Pro  Asn  Gly  Ala  Glu  Ala  Ala  Gln  Arg  Ser  Leu  Gly
  1              5                        10                       15
Gly  Gly  Ala  Ser  Arg  Pro  Arg  Ala  Ala  Leu  Ala  Glu  Gly  Gly  Gly  Ala
                20                       25                       30
Gly  Glu  Glu  Pro  Gly  Ala  Ala  Ala  Glu  Ala  Gly  Arg  Arg  Arg  Gly  Pro
            35                       40                       45
Leu  Pro  Leu  Glu  Asp  Pro  Ala  Glu  Met  Leu  Ala  Glu  Asn  Leu  Val  Glu
       50                       55                       60
Glu  Phe  Glu  Met  Lys  Glu  Asp  Glu  Pro  Trp  Tyr  Asp  His  Gln  Asp  Leu
 65                       70                       75                       80
Gln  Gln  Asp  Leu  Gln  Leu  Ala  Ala  Glu  Leu  Gly  Lys  Thr  Leu  Leu  Asp
                85                       90                       95
Arg  Asn  Thr  Glu  Leu  Glu  Asp  Ser  Val  Gln  Gln  Met  Tyr  Thr  Thr  Asn
             100                      105                      110
Gln  Glu  Gln  Leu  Gln  Glu  Ile  Glu  Tyr  Leu  Thr  Lys  Gln  Val  Glu  Leu
            115                      120                      125
Leu  Arg  Gln  Met  Asn  Glu  Gln  His  Ala  Lys  Val  Tyr  Glu  Gln  Leu  Asp
      130                      135                      140
Val  Thr  Ala  Arg  Glu  Leu  Glu  Glu  Thr  Asn  Gln  Lys  Leu  Val  Ala  Asp
145                      150                      155                      160
Ser  Lys  Ala  Ser  Gln  Gln  Lys  Ile  Leu  Ser  Leu  Thr  Glu  Thr  Ile  Glu
                165                      170                      175
Cys  Leu  Gln  Thr  Asn  Ile  Asp  His  Leu  Gln  Ser  Gln  Val  Glu  Glu  Leu
            180                      185                      190
Lys  Ser  Ser  Gly  Gln  Gly  Arg  Arg  Ser  Pro  Gly  Lys  Cys  Asp  Gln  Glu
           195                      200                      205
```

-continued

```
Lys  Pro  Ala  Pro  Ser  Phe  Ala  Cys  Leu  Lys  Glu  Leu  Tyr  Asp  Leu  Arg
     210                 215                 220
Gln  His  Phe  Val  Tyr  Asp  His  Val  Phe  Ala  Glu  Lys  Ile  Thr  Ser  Leu
225                      230                 235                           240
Gln  Gly  Gln  Pro  Ser  Pro  Asp  Glu  Glu  Asn  Glu  His  Leu  Lys  Lys
                    245                 250                      255
Thr  Val  Thr  Met  Leu  Gln  Ala  Gln  Leu  Ser  Leu  Glu  Arg  Gln  Lys  Arg
               260                 265                      270
Val  Thr  Met  Glu  Glu  Glu  Tyr  Gly  Leu  Val  Leu  Lys  Glu  Asn  Ser  Glu
               275                 280                      285
Leu  Glu  Gln  Gln  Leu  Gly  Ala  Thr  Gly  Ala  Tyr  Arg  Ala  Arg  Ala  Leu
     290                 295                      300
Glu  Leu  Glu  Ala  Glu  Val  Ala  Glu  Met  Arg  Gln  Met  Leu  Gln  Ser  Glu
305                      310                 315                           320
His  Pro  Phe  Val  Asn  Gly  Val  Glu  Lys  Leu  Val  Pro  Asp  Ser  Leu  Tyr
                    325                 330                      335
Val  Pro  Phe  Lys  Glu  Pro  Ser  Gln  Ser  Leu  Leu  Glu  Glu  Met  Phe  Leu
               340                 345                      350
Thr  Val  Pro  Glu  Ser  His  Arg  Lys  Pro  Leu  Lys  Arg  Ser  Ser  Ser  Glu
          355                      360                 365
Thr  Ile  Leu  Ser  Ser  Leu  Ala  Gly  Ser  Asp  Ile  Val  Lys  Gly  His  Glu
     370                 375                      380
Glu  Thr  Cys  Ile  Arg  Arg  Ala  Lys  Ala  Val  Lys  Gln  Arg  Gly  Ile  Ser
385                      390                 395                           400
Leu  Leu  His  Glu  Val  Asp  Thr  Gln  Tyr  Ser  Ala  Leu  Lys  Val  Lys  Tyr
               405                 410                      415
Glu  Glu  Leu  Leu  Lys  Lys  Cys  Gln  Glu  Gln  Asp  Ser  Leu  Ser  His
                    420                 425                 430
Lys  Ala  Gly  Arg  Pro  Pro  Gly  Cys  Ser  Gln  Gly  Pro  Asp  Trp  Ser  Asp
               435                 440                      445
Ala  Gln  Ser  Glu  Pro  Val  Ala  Ser  Gly  Trp  Glu  Leu  Ala  Ser  Val  Asn
     450                      455                 460
Pro  Glu  Pro  Val  Ser  Ser  Pro  Thr  Thr  Pro  Pro  Glu  Tyr  Lys  Ala  Leu
465                      470                      475                      480
Phe  Lys  Glu  Ile  Phe  Ser  Cys  Ile  Lys  Lys  Thr  Lys  Gln  Glu  Ile  Asp
               485                      490                      495
Glu  Gln  Arg  Thr  Lys  Tyr  Arg  Ser  Leu  Ser  Ser  His  Ser
               500                 505
```

( 2 ) INFORMATION FOR SEQ ID NO:2:

( i ) SEQUENCE CHARACTERISTICS:
        ( A ) LENGTH: 2333 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: N ( i v ) ANTI-SENSE: N ( v i i ) IMMEDIATE SOURCE:
        ( B ) CLONE: Py2

( x i ) SEQUENCE DESCRIPTION: SEQ ID NO:2:

```
TCCCCGCAAG ATCTTCAACT TGCTGCTGAG CTTGGGAAGA CATTACTGGA TCGGAACACA        60
GAGTTGGAGG ACTCTGTTCA GCAGATGTAT ACAACCAATC AGGAGCAGTT ACAGGAAATT       120
```

-continued

```
GAGTATCTGA CGAAGCAAGT GGAACTTCTA CGGCAGATGA ACGAACAACA TGCAAAGGTT    180
TATGAACAAT TAGACGTCAC AGCAAGGGAA CTGGAAGAAA CAAATCAAAA GCTAGTTGCT    240
GACAGCAAGG CCTCACAGCA AAGATTCTG AGCCTGACTG AAACGATTGA ATGCCTGCAA     300
ACCAACATTG ATCACCTCCA GAGCCAAGTG GAGGAGCTGA AGTCATCTGG CCAAGGGAGA    360
AGGAGCCCGG GAAAGTGTGA CCAGGAGAAA CCGGCACCCA GCTTTGCATG TCTGAAGGAG    420
CTGTATGACC TCCGCCAACA CTTCGTGTAT GATCATGTGT TCGCTGAGAA GATCACTTCC    480
TTGCAAGGTC AGCCAAGCCC TGATGAAGAG AAAATGAGC ACTTGAAAAA AACAGTGACA     540
ATGTTGCAGG CCCAGCTGAG CCTGGAGCGG CAGAAGCGGG TGACTATGGA GGAGGAATAT    600
GGGCTCGTGT TAAAGGAGAA CAGTGAACTG GAGCAGCAGC TGGGGGCCAC AGGTGCCTAC    660
CGAGCACGGG CGCTGGAACT AGAGGCCGAG GTGGCAGAGA TGCGACAGAT GTTGCAGTCA    720
GAGCATCCAT TTGTGAATGG AGTTGAGAAG CTGGTGCCAG ACTCTCTGTA TGTTCCTTTC    780
AAAGAGCCCA GCCAGAGCCT GCTGGAAGAG ATGTTCCTGA CTGTGCCGGA ATCACATAGA    840
AAGCCTCTCA AGCGCAGCAG CAGTGAGACG ATCCTCAGCA GCTTGGCAGG GAGTGACATC    900
GTGAAGGGCC ACGAGGAGAC CTGCATCAGG AGGGCCAAGG CTGTGAAACA GAGGGGCATC    960
TCCCTTCTGC ACGAAGTGGA CACGCAGTAC AGCGCCCTGA AGGTGAAGTA TGAAGAGTTG    1020
CTGAAGAAGT GCCAAGAGGA ACAGGACTCC CTGTCACACA AGGCTGGCAG ACCTCCAGGC    1080
TGCAGCCAAG GACCTGACTG GAGTGACGCC CAGTCTGAGC CTGTTGCCAG CGGCTGGGAA    1140
CTGGCCTCTG TCAACCCAGA GCCCGTGAGT TCCCTACAA CACCTCCAGA ATACAAAGCG     1200
TTGTTTAAGG AGATCTTTAG TTGCATCAAG AAAACTAAGC AGGAAATAGA TGAACAGAGA    1260
ACAAAATACC GATCACTCTC CTCTCATTCT TAATTGACCT CTAGCTCTAC TACTAATTTG    1320
CCTATTGCCT ATCGCCTCTC TCCCATTCAG ACAAGTGTTT GTAGACTCTG AAGCCTAATG    1380
TTACTCATGA CGTTTGCCTC ATTGCTTTGC TTATTTAGCA AATGCATACA ACGAGGAAAG    1440
GAGGTGGCTA GTGGTATCAG TTCTCTGATC CACTTCCATT TAACCTCCCC AGGAAATCCC    1500
ATGACAAACT GGCCTCTGGC TGGCGCGCTG ATTAGACTTC AGTTCCTGAA AAGGACCAGT    1560
GGAGGGAAGA GCTATACTTC TGGAGAAGTA GGCCTGGAGT TACTACAGTA TGGGGGAAAA    1620
GGGTCGAGTT AGAACAAAGC TAAGGCAATT CCTATTGCTT CCTTGCGCAA CTTCTCAAAA    1680
CGATGAAAGT CAGAAGGCTG TCAAACTCAA ATATCTTTGC AAACACTGTT TGAATACTGT    1740
GAATTCTTCA TTACGAAGAA TGTTCGAGAG AAAGCAGGGG TCTAATCCAA AAGAAATGTC    1800
ATTAACCAAT ACTCCAAGTC CTTGAGTTTT GTTATATCTG AACTAGTTGA ACTGTGACTG    1860
ACAGGTAATC CTAATATATC CAAATCCAAC TGAATACCAA ATTGAGATGG CAAATTTTTG    1920
TTTGATATAA GTTAGCTTGT TAGCATATGC CCTAGAGGGC CTCCATCCCT GATTCTAATG    1980
TTTTTACTCA AAGCTCTAGC CTTTAGGATA GGTGAATATG TAAATCTTTT ATCACTTTCT    2040
CAAATTCAAA CTAAAGGGGA AAGATCAAAC CCCTTCCCTT CCTACCTGTT TTCTGAGCTG    2100
GCTGACTTGC CAGCCACAAG CTGCTCTTGC AGAGTTCTTA CCATTCCTGT AAATGTTTTG    2160
ACTTGTTGCA GAAATTCCTA TCTACTTTAT TAAGCAGTAT TGATCTGACT GTGGAAACAT    2220
CCTCTCACTT GCATTCTTTT AACTTAAAAC TATTTAAGAA CTGATGTTCC GATTATTGTA    2280
TATATTTTTC TAAAAACCAA ATAAAGCTAC CTATGAAAGG AATTCCGGAA TTC           2333
```

( 2 ) INFORMATION FOR SEQ ID NO:3:

( i ) SEQUENCE CHARACTERISTICS:
        ( A ) LENGTH: 4 amino acids (B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:3:

Ser Pro Lys Lys
1

(2) INFORMATION FOR SEQ ID NO:4:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:4:

Leu Gln Thr Glu Ile Ala Asn Leu
1               5

(2) INFORMATION FOR SEQ ID NO:5:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:5:

Leu Leu Glu Asp Val Glu
1               5

(2) INFORMATION FOR SEQ ID NO:6:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:6:

```
    Phe  Leu  Glu  Asp  Val  Glu
    1              5
```

( 2 ) INFORMATION FOR SEQ ID NO:7:

( i ) SEQUENCE CHARACTERISTICS:
        ( A ) LENGTH: 430 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:7:

```
    Ser  Pro  Gln  Asp  Leu  Gln  Leu  Ala  Ala  Glu  Leu  Gly  Lys  Thr  Leu  Leu
    1              5                        10                       15

Asp  Arg  Asn  Thr  Glu  Leu  Glu  Asp  Ser  Val  Gln  Gln  Met  Tyr  Thr  Thr
                   20                       25                       30

Asn  Gln  Glu  Gln  Leu  Gln  Glu  Ile  Glu  Tyr  Leu  Thr  Lys  Gln  Val  Glu
                   35                       40                       45

Leu  Leu  Arg  Gln  Met  Asn  Glu  Gln  His  Ala  Lys  Val  Tyr  Glu  Gln  Leu
         50                       55                       60

Asp  Val  Thr  Ala  Arg  Glu  Leu  Glu  Glu  Thr  Asn  Gln  Lys  Leu  Val  Ala
    65                       70                       75                       80

Asp  Ser  Lys  Ala  Ser  Gln  Gln  Lys  Ile  Leu  Ser  Leu  Thr  Glu  Thr  Ile
                            85                       90                       95

Glu  Cys  Leu  Gln  Thr  Asn  Ile  Asp  His  Leu  Gln  Ser  Gln  Val  Glu  Glu
                   100                      105                      110

Leu  Lys  Ser  Ser  Gly  Gln  Gly  Arg  Arg  Ser  Pro  Gly  Lys  Cys  Asp  Gln
                   115                      120                      125

Glu  Lys  Pro  Ala  Pro  Ser  Phe  Ala  Cys  Leu  Lys  Glu  Leu  Tyr  Asp  Leu
         130                      135                      140

Arg  Gln  His  Phe  Val  Tyr  Asp  His  Val  Phe  Ala  Glu  Lys  Ile  Thr  Ser
    145                      150                      155                      160

Leu  Gln  Gly  Gln  Pro  Ser  Pro  Asp  Glu  Glu  Glu  Asn  Glu  His  Leu  Lys
                            165                      170                      175

Lys  Thr  Val  Thr  Met  Leu  Gln  Ala  Gln  Leu  Ser  Leu  Glu  Arg  Gln  Lys
                   180                      185                      190

Arg  Val  Thr  Met  Glu  Glu  Glu  Tyr  Gly  Leu  Val  Leu  Lys  Glu  Asn  Ser
         195                      200                      205

Glu  Leu  Glu  Gln  Gln  Leu  Gly  Ala  Thr  Gly  Ala  Tyr  Arg  Ala  Arg  Ala
         210                      215                      220

Leu  Glu  Leu  Glu  Ala  Glu  Val  Ala  Glu  Met  Arg  Gln  Met  Leu  Gln  Ser
    225                      230                      235                      240

Glu  His  Pro  Phe  Val  Asn  Gly  Val  Glu  Lys  Leu  Val  Pro  Asp  Ser  Leu
                            245                      250                      255

Tyr  Val  Pro  Phe  Lys  Glu  Pro  Ser  Gln  Ser  Leu  Leu  Glu  Glu  Met  Phe
                   260                      265                      270

Leu  Thr  Val  Pro  Glu  Ser  His  Arg  Lys  Pro  Leu  Lys  Arg  Ser  Ser  Ser
                   275                      280                      285

Glu  Thr  Ile  Leu  Ser  Ser  Leu  Ala  Gly  Ser  Asp  Ile  Val  Lys  Gly  His
         290                      295                      300

Glu  Glu  Thr  Cys  Ile  Arg  Arg  Ala  Lys  Ala  Val  Lys  Gln  Arg  Gly  Ile
```

-continued

| 305 | | | | | | | | | 315 | | | | 320 |
|---|---|---|---|---|---|---|---|---|---|---|---|---|---|
| Ser | Leu | Leu | His | Glu 325 | Val | Asp | Thr | Gln | Tyr 330 | Ser | Ala | Leu | Lys | Val 335 | Lys |
| Tyr | Glu | Glu | Leu 340 | Leu | Lys | Lys | Cys | Gln 345 | Glu | Glu | Gln | Asp | Ser 350 | Leu | Ser |
| His | Lys | Ala 355 | Gly | Arg | Pro | Pro | Gly 360 | Cys | Ser | Gln | Gly | Pro 365 | Asp | Trp | Ser |
| Asp | Ala 370 | Gln | Ser | Glu | Pro | Val 375 | Ala | Ser | Gly | Trp | Glu 380 | Leu | Ala | Ser | Val |
| Asn 385 | Pro | Glu | Pro | Val | Ser 390 | Ser | Pro | Thr | Thr | Pro 395 | Pro | Glu | Tyr | Lys | Ala 400 |
| Leu | Phe | Lys | Glu | Ile 405 | Phe | Ser | Cys | Ile | Lys 410 | Lys | Thr | Lys | Gln | Glu 415 | Ile |
| Asp | Glu | Gln | Arg 420 | Thr | Lys | Tyr | Arg | Ser 425 | Leu | Ser | Ser | His | Ser 430 | | |